(12) United States Patent
Ebara et al.

(10) Patent No.: US 6,491,669 B2
(45) Date of Patent: Dec. 10, 2002

(54) PROTECTOR FOR LIQUID DRUG ADMINISTRATION NEEDLE

(75) Inventors: Yukinori Ebara, Osaka (JP); Naohiro Atsumi, Osaka (JP); Hidekazu Miyauchi, Osaka (JP); Atsushi Ichimiya, Osaki (JP)

(73) Assignee: Nipro Corporation, Osaka-fu (JP)

( * ) Notice: Subject to any disclaimer, the term of this patent is extended or adjusted under 35 U.S.C. 154(b) by 0 days.

(21) Appl. No.: 09/929,100

(22) Filed: Aug. 15, 2001

(65) Prior Publication Data

US 2002/0026153 A1 Feb. 28, 2002

(30) Foreign Application Priority Data

Aug. 28, 2000 (JP) ........................................ 2000-257002

(51) Int. Cl.$^7$ ............................. A61M 5/00; A61M 5/32
(52) U.S. Cl. ...................................... 604/263; 604/162
(58) Field of Search ................................ 604/162, 167, 604/174, 177, 192, 197, 198, 263

(56) References Cited

U.S. PATENT DOCUMENTS

| 4,631,058 | A | | 12/1986 | Raines |
| 4,743,231 | A | | 5/1988 | Kay et al. |
| 4,928,824 | A | | 5/1990 | Barasch |
| 5,304,148 | A | * | 4/1994 | Lannoye et al. ............ 604/192 |
| 5,368,575 | A | * | 11/1994 | Chang ........................ 604/174 |
| 5,738,220 | A | * | 4/1998 | Geszler ...................... 206/726 |

FOREIGN PATENT DOCUMENTS

EP 0 425 448 A2 9/1990

* cited by examiner

Primary Examiner—Sharon Kennedy
(74) Attorney, Agent, or Firm—Birch, Stewart, Kolasch & Birch, LLP

(57) ABSTRACT

A protector for housing a drug administration needle comprised of a winged hub and a cannula bent substantially perpendicular to a longitudinal axis of the hub at a longitudinal central portion of the hub. The protector comprises a tubular cannula-protecting portion having a cannula entrance at one end and a bottom at the opposite end; and a hub-mounting portion for attachment of the winged hub, the hub-mounting portion being coaxially formed on the cannula entrance of the cannula-protecting portion.

5 Claims, 7 Drawing Sheets

PROTECTOR FOR LIQUID DRUG ADMINISTRATION NEEDLE

BACKGROUND OF THE INVENTION

The present invention relates to a protector for a liquid drug administration needle used for percutaneous infusion of a liquid drug into an implantable catheter which comprises an infusion catheter attached to a reservoir and is suitable for administration of a liquid drug to a patient over a long period of time.

When a liquid drug has to be administered over a long period of time, it is general practice to use a so-called implantable catheter, which is basically comprised of a reservoir to be implanted just under the skin at an appropriate site in a patient's body, and an infusion catheter attached to the reservoir for introducing the liquid drug contained in the reservoir into a selected administration site in a patient's body. The reservoir is provided with a septum of an elastic material, which is capable of being pierced by a cannula of a liquid drug administration needle and of sealing itself when the cannula is taken out therefrom. The implantable catheter is implanted in the body so that the septum is situated just under the skin and approximately parallels to the skin surface. Thus, when introducing a liquid drug into the reservoir, it is sufficient to insert the cannula of the liquid drug administration needle connected to a drug container or the like into the reservoir through the patient's skin and the septum.

The liquid drug administration needle which introduces the liquid drug into the implantable catheter is bent at an angle of 90 degrees to its longitudinal axis to make it convenient for needle penetration to the septum located parallel to the skin surface, i.e., to assure a correct penetration of the cannula at right angles to the skin. The liquid drug administration needles with a 90 degree-bend, made by bending a cannula protruded from a distal end of a needle hub, provide easier use as compared to the straight needles when applied to the implanted catheter, but it is troublesome to insert the cannula in the septum since the piercing position of the cannula is out of alignment with the needle grasp. Further, since the piercing position of the cannula is out of the fixed position of the hub, when the patient moves, deviation can occur between the hub and the reservoir. This causes fluctuations of the puncture depth of the cannula, resulting in increase of the risk of infection at the penetration site of the cannula. Further, with the liquid drug administration needles of the prior art, it is difficult to avoid accidental pricking of user's finger with a needle when a physician intends to attach a protector on the liquid drug administration needle used for any patient, or to throw out the used liquid drug administration needle.

To solve such problems, a drug administration needle unit has been proposed that comprises a tabular base 120, a raised boss 160 provided on the central part of the base 120, a needle or cannula 140 bent at an angle of 90 degrees in the middle portion of the boss 160 and projected from the base 120, a handle 420 which facilitates inserting needle 140 into and withdrawing it from the patient, and a rigid protective cover 380 for protecting needle 140 (U.S. Pat. No. 4,743,231). In this needle unit, however, a pad 240 is used for holding the unit on the skin of the patient when the needle unit is inserted in the patient, so that it causes increase in production cost as compared with the conventional winged drug administration needles. In addition, the needle unit becomes large in size as a whole and takes a lot of trouble with attachment or displacement of the protective cover 380 since the protective cover 380 is so designed as to be attached to the base 120 to enclose the needle 140 and the pad 240.

SUMMARY OF THE INVENTION

It is therefore an object of the present invention to provide a protector for a liquid drug administration needle, which is relatively compact and advantageous cost and makes it possible to prevent accidental pricking of user's finger with the needle, which may occur when applying it to an implantable catheter or discarding the used needle.

According to the present invention, the above object is achieved by employing a cannula bent at an angle of 90 egrees in the central portion of a winged hub like as the drug infusion needle of U.S. Pat. No. 4,743,231, aligning the axis of the cannula and an axis of a force applied to the hub by fingers when fitting on or taking out from the protector, and providing means for fixing the winged hub on the protector.

According to the present invention, there is provided a protector for housing a cannula of a drug administration needle, said needle comprising a winged hub and a cannula bent substantially perpendicular to an longitudinal axis of the hub at a longitudinal central portion of the hub, said protector comprising:

a tubular cannula-protecting portion having a cannula entrance at one end and a bottom at the opposite end; and a hub-mounting portion for attachment of said winged hub, said hub-mounting portion being coaxially formed on the cannula entrance of the cannula-protecting portion.

The hub-mounting portion may be formed directly on the edge of the cannula entrance or on a flange, which has been provided on the cannula entrance to ensure prevention of the accidental pricking with the needle. The hub-mounting portion may comprise a pair of arch-shaped members with hub-engaging means on its inner wall, so that the winged hub for drug administration needle is clamped between said arch-shaped members. The cannula-protecting portion may be provided on an outside thereof with a covering portion to cover the cannula deviated from the cannula entrance.

Further scope of applicability of the present invention will become apparent form the detailed description given hereinafter. However, it should be understood that the detailed description and specific example, while indicating preferred embodiments of the invention, are given by way of illustration only; since various changes and modifications within the spirit an scope of the invention will become apparent to those skilled in he art form the detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION.

Figure 1:
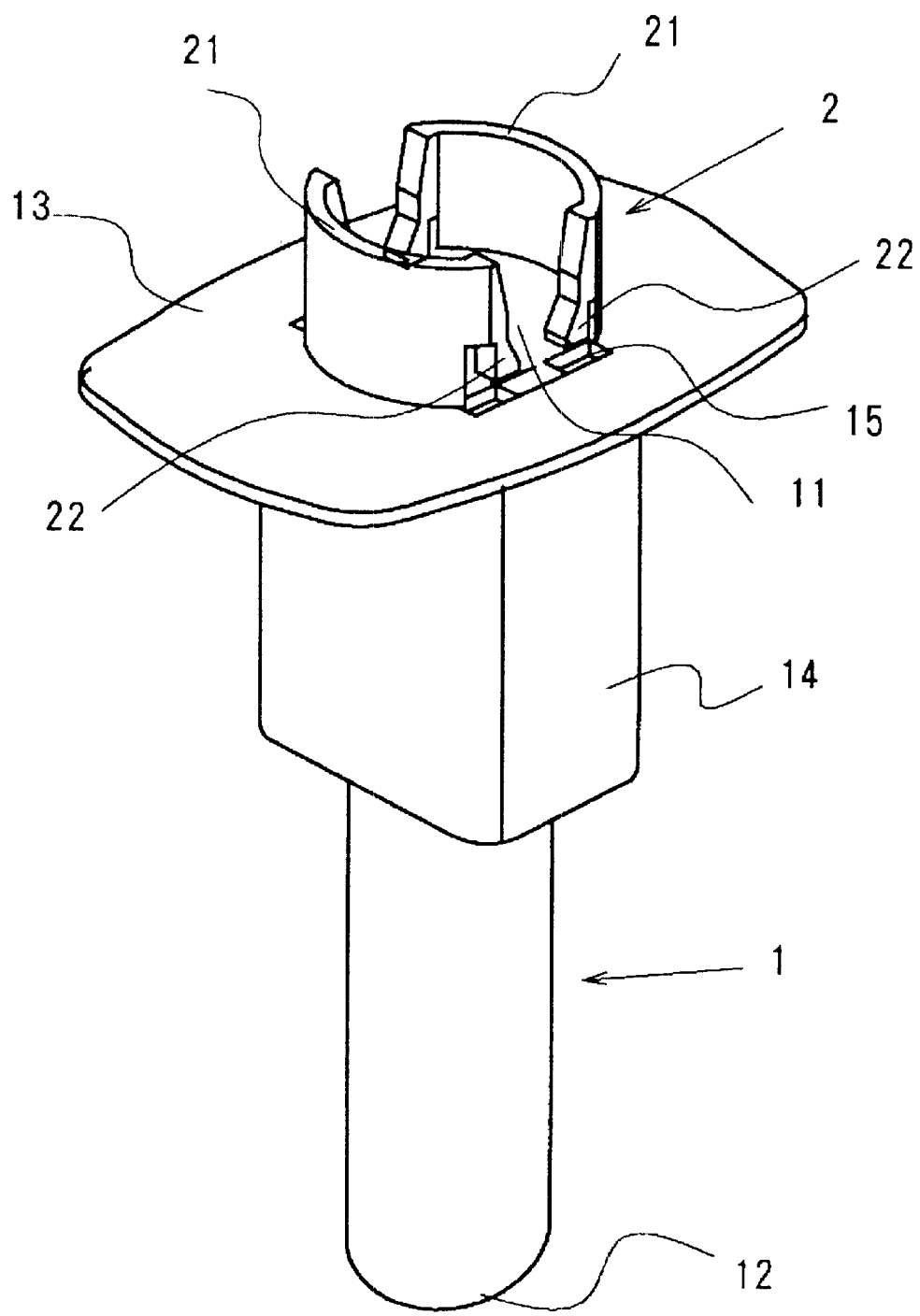
FIG. 1 is an oblique view of a protector according to one embodiment of the present invention.
Figure 2:
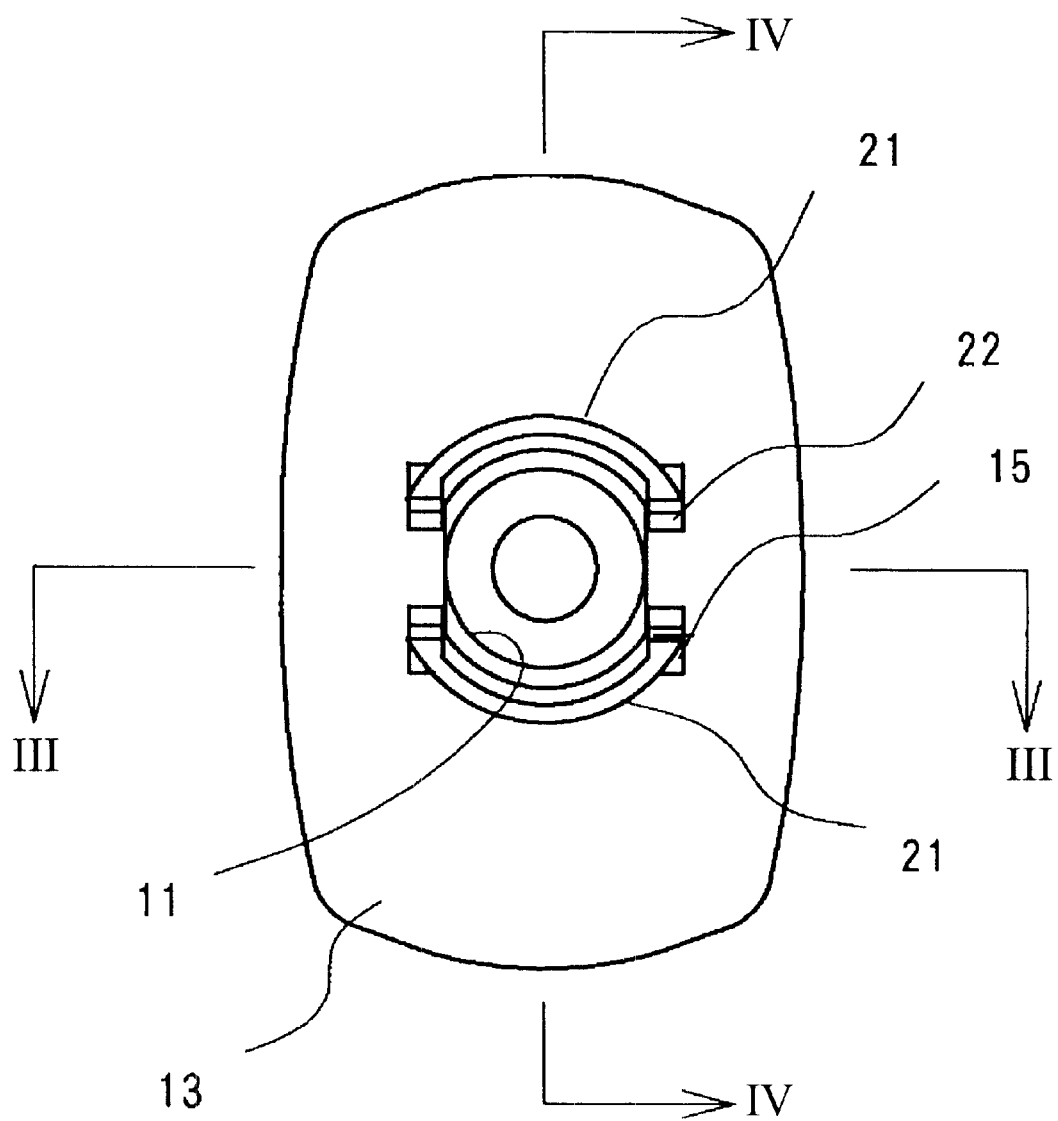
FIG. 2 is a plan view of the protector shown in FIG. 1.
Figure 5:
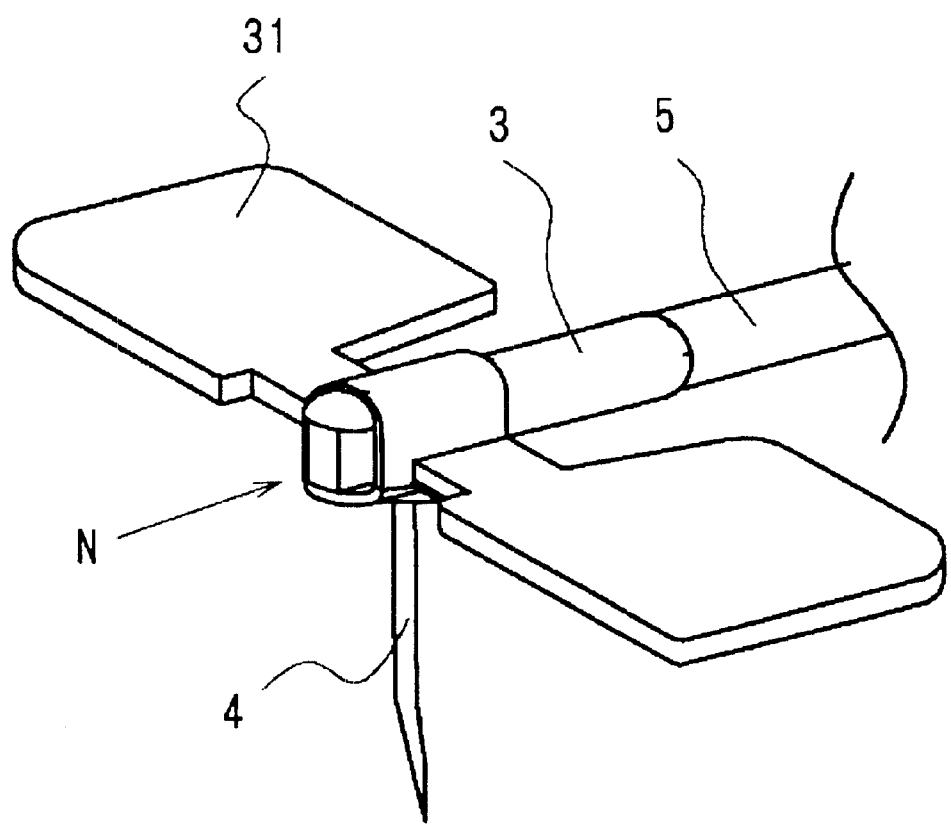
FIG. 5 is an oblique view of a drug administration needle applied to the protector of the present invention.
Figure 6:
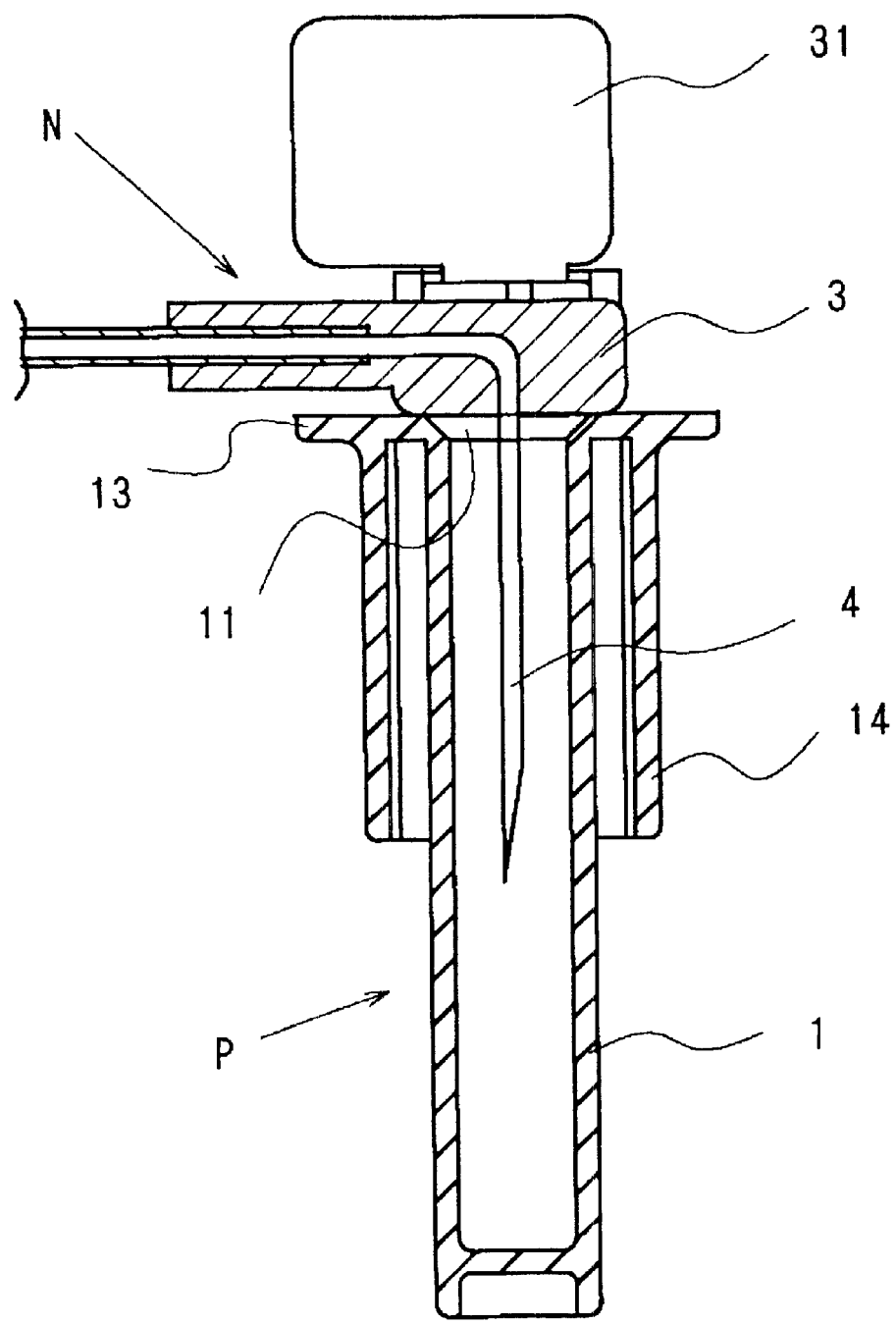
FIG. 6 is a vertical cross section of the protector shown in FIG. 1 with the drug administration needle attached thereto, taken along a line passing through an axis of a hub.
Figure 7:
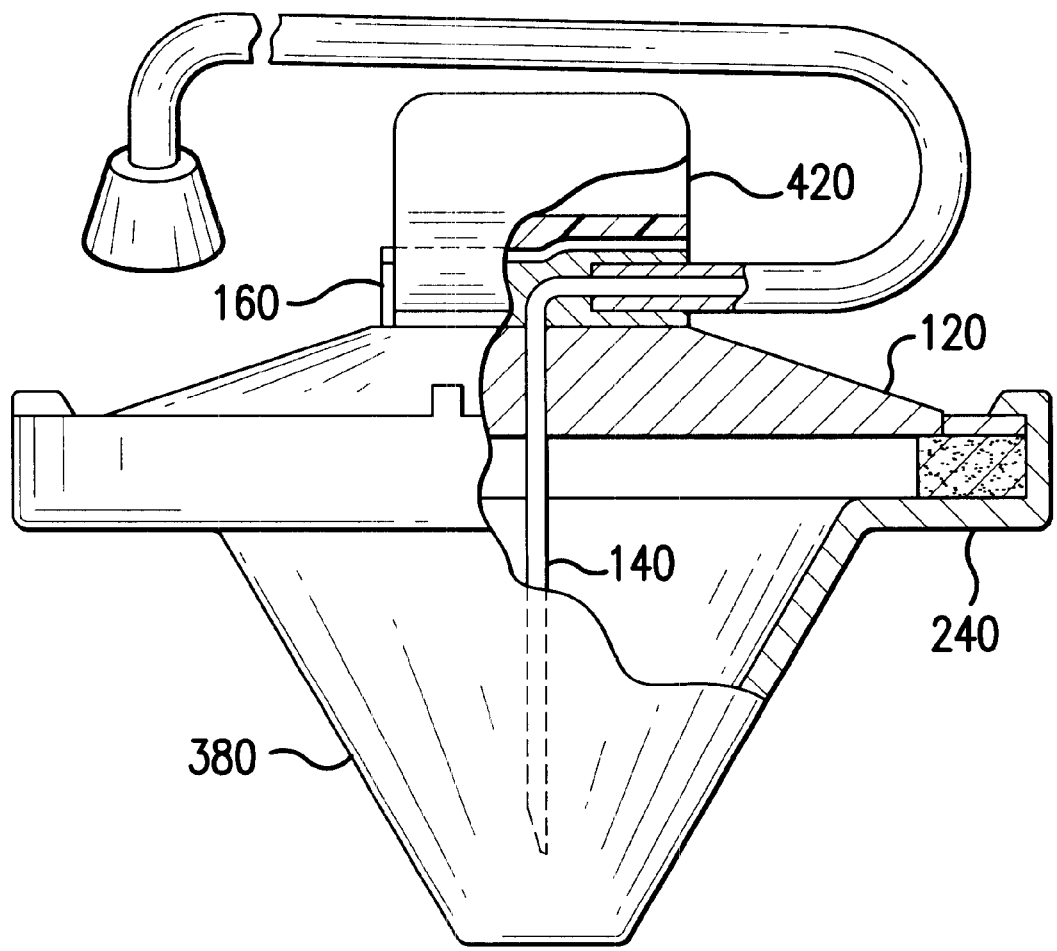
FIG. 7 is a partially cut-away elevation view of a protector of the prior art.

Referring now to FIG. 1, there is shown a protector according to the present invention designed to hold a cannula 4 of a drug administration needle N which, as illustrated in FIG. 5, comprises a hub 3 with a wing 31 and a cannula 4 held therein and bent in the direction substantially perpendicular to the axis of the hub 3 at a longitudinal central portion of the hub 3. As illustrated in FIG. 1, the needle protector comprises a tubular cannula-protecting portion 1 having a cannula entrance 11 at one end and a bottom 12 at the opposite end, and a hub-mounting portion 2 formed coaxial to the cannula-protecting portion 1 round the cannula entrance 11 thereof for attachment of the winged hub 3. In order to ensure protection from accidental needlesticks, the cannula entrance 11 may be provided with a flange 13.

Figure 3:
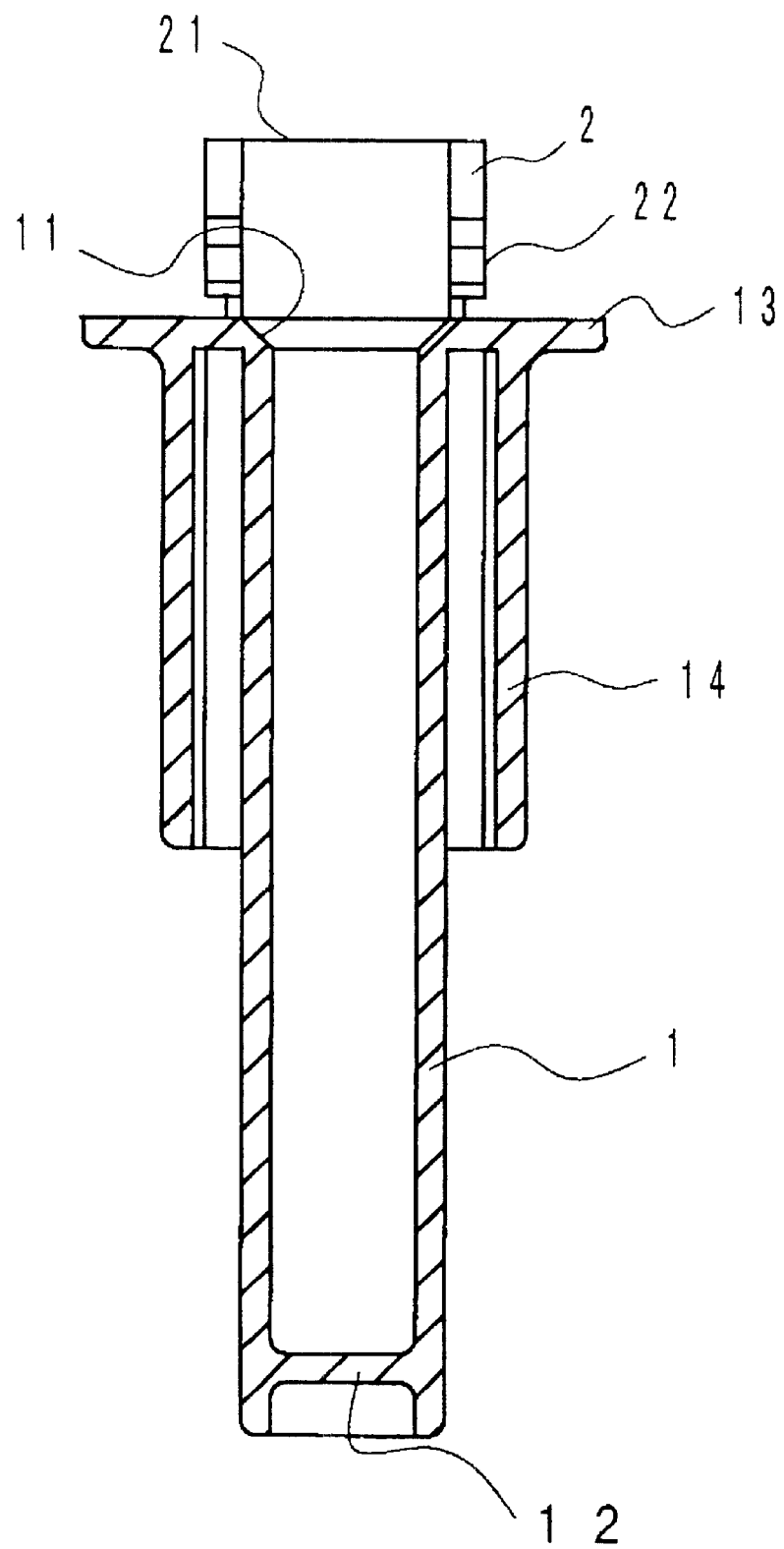
FIG. 3 is a cross section taken along a line III—III in FIG. 2.
Figure 4:
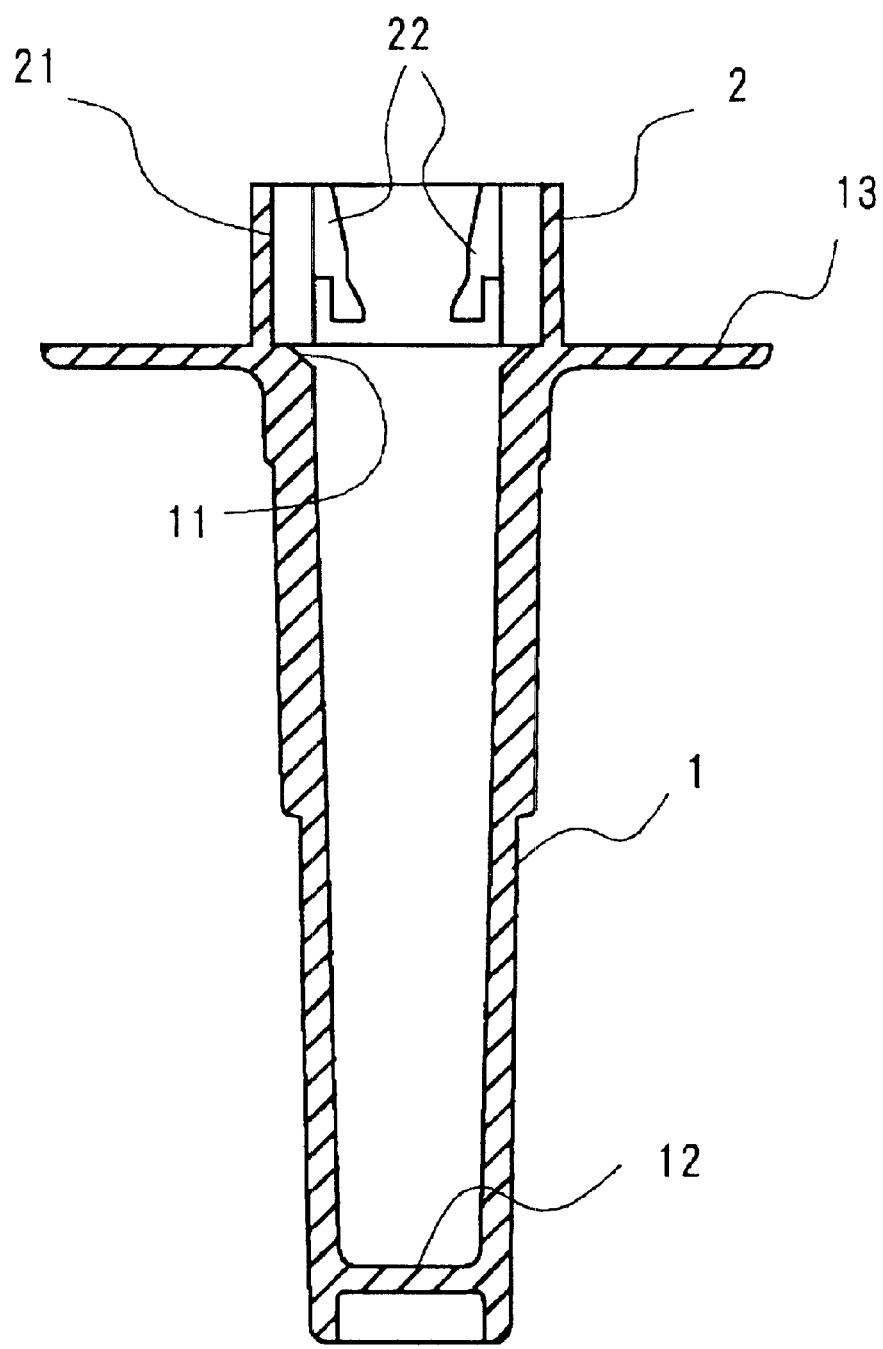
FIG. 4 is a cross section taken along a line IV—IV in FIG. 2.

As illustrated in FIGS. 3 and 4, the cannula-protecting portion 1 is formed in a tubular shape and has a cannula entrance 11 and a bottom 12. In order to prevent accidental needlesticks which may occur, for example, when a flange 13 is provided with an air vent 15 for letting out air during molding, the cannula-protecting portion 1 may be provided with a covering portion 14 extending from the external wall of the cannula entrance 11 towards the bottom 12. The covering portion 14 houses the cannula 4 deviated from the cannula entrance 11 and inserted into the air vent hole 15.

The cannula-protecting portion 1 is provided on the open end thereof with a flange 13 on which the hub-mounting portion 2 is provided so as to surround the cannula entrance 11, as shown in FIGS. 3 and 4. Alternatively, the hub-mounting portion 2 may be provided directly on the open end of the cannula-protecting portion 1. The hub-mounting portion 2 comprises a pair of arch-shaped members 21, 21, which are respectively provided on inner walls thereof with hub-engaging means, to hold the winged hub 3 of the drug administration needle N between said pair of arch-shaped members 21, 21. As the hub-engaging means, there may be used a pair of flexible engaging hooks 22, 22 of a cantilever type attached to a flat end of the sidewall of the arch-shaped members 21, 21. A distance between opposing flexible engaging hooks 22, 22 of the arch-shaped members 21, 21 is so determined that it is smaller than a diameter of the hub 3 in the normal state but becomes larger than the diameter of the hub 3 when the arch-shaped members 21, 21 are bent outward.

The protector of the present invention is combined with the drug administration needle N as illustrated in FIG. 5. The drug administration needle N comprises a hub 3 provided with a wing 31, and a cannula 4 arranged therein and bent at a longitudinal central portion of the hub 3 in the direction substantially perpendicular to the axis of the hub 3. In the drawings, reference numeral 5 indicates a tube-connecting portion provided at a proximal end of the hub 3, in which the needle 4 is connected to a tube 6.

In use, the drug administration needle N is attached to the protector by picking the wing 31 of the needle N with fingers and inserting the hub 3 in the hub-mounting portion 2 of the protector P so that the pointed end of the cannula 4 is located on the axis of cannula entrance 11. By thrusting the hub 3 into the space between arch-shaped members 21, 21, the flexible engaging hooks 22, 22 are bent outward and the distance between the flexible engaging hooks 22, 22 is lengthened to the diameter of the hub 3. Thus, the hub 3 is further thrusted toward the cannula-protecting portion 1 and then caught by the flexible engaging hooks 22, 22.

As will be understood from the above, the protector for a liquid drug administration needle according to the present invention is relatively compact and has the advantage of low production cost as compared with the conventional products. Further, since the holding position of the wing is present on the axis of the cannula, it is easy to perform insertion and removal of the drug administration needle. In addition, it is possible to prevent the user form accidental needlesticks at the time of application to the implanted catheter or discard of the used needles since the protector has a construction which prevents the needle from slipping out of the engaging hooks.

What is claimed is:

1. A protector for housing a cannula for a drug administration needle, said needle comprising:

a winged hub and a cannula bent substantially perpendicular to a longitudinal axis of the hub at a longitudinal center portion of the hub, said protector comprising:

a tubular cannula-protecting portion having a cannula entrance at one end and a bottom at the opposite end; and a hub-mounting portion for attachment of said winged hub, said hub-mounting portion being coaxially formed on the cannula entrance of the cannula-protecting portion.

2. The protector according to claim 1, wherein the hub-mounting portion is formed directly on the edge of the cannula entrance.

3. The protector according to claim 1, wherein the hub-mounting portion is formed on a flange provided on the cannula entrance.

4. The protector according to claim 1, wherein the hub-mounting portion comprises a pair of arch-shaped members with hub-engaging means on its inner wall, and wherein the winged hub for drug administration needle is clamped between said arch-shaped members.

5. The protector according to claim 1, wherein the cannula-protecting portion may be provided on an outside thereof with a covering portion to cover the cannula deviated from the cannula entrance.

* * * * *